(12) United States Patent
Krattiger

(10) Patent No.: US 8,372,004 B2
(45) Date of Patent: Feb. 12, 2013

(54) SPECKLE REDUCTION OF MICROWHITE ENDOSCOPES

(75) Inventor: Beat Krattiger, Beringen (CH)

(73) Assignee: Storz Endoskop Produktions GmbH (DE)

( * ) Notice: Subject to any disclaimer, the term of this patent is extended or adjusted under 35 U.S.C. 154(b) by 370 days.

(21) Appl. No.: 12/762,138

(22) Filed: Apr. 16, 2010

(65) Prior Publication Data

US 2010/0268034 A1    Oct. 21, 2010

(30) Foreign Application Priority Data

Apr. 17, 2009 (DE) .................. 10 2009 017 940

(51) Int. Cl.
*A61B 1/06* (2006.01)
(52) U.S. Cl. ...................................... 600/178
(58) Field of Classification Search .................. 600/178, 600/160
See application file for complete search history.

(56) References Cited

U.S. PATENT DOCUMENTS

| | | | |
|---|---|---|---|
| 4,011,403 A | | 3/1977 | Epstein et al. |
| 5,471,545 A | * | 11/1995 | Negami et al. ............ 385/1 |
| 6,040,910 A | | 3/2000 | Wu et al. |
| 8,175,685 B2 | * | 5/2012 | Yun et al. ............ 600/473 |
| 2003/0007714 A1 | | 1/2003 | Park |
| 2006/0085969 A1 | | 4/2006 | Bennett et al. |
| 2006/0198418 A1 | | 9/2006 | Hama et al. |
| 2006/0279950 A1 | | 12/2006 | Hama et al. |
| 2007/0238955 A1 | * | 10/2007 | Tearney et al. ............ 600/407 |
| 2008/0089089 A1 | | 4/2008 | Hama et al. |
| 2010/0210911 A1 | * | 8/2010 | Shimotsu ............ 600/178 |
| 2010/0220293 A1 | * | 9/2010 | Mizushima et al. ............ 353/20 |

FOREIGN PATENT DOCUMENTS

| | | |
|---|---|---|
| JP | 2005205195 A | 8/2005 |
| WO | 2009021079 A1 | 2/2009 |
| WO | 2009034694 A1 | 3/2009 |

OTHER PUBLICATIONS

Benjamin Dingel and Satoshi Kawata, Laser-diode microsope with fiber illumination, Optics Communication vol. 93, No. 2, 2 (1992) pp. 27-32.*
European Search Report; Application No. EP 10 00 3569; Aug. 12, 2010; 7 pages.
Iwai, et al.; "Speckle Reduction in Coherent Information Processing"; Proceedings of the IEEE; New York, Issue Date: May 1996; vol. 84 Issue 5; pp. 765-781 (abstract only).
Nonlinear Dynamics and Chaos, by J.M.T. Thomson and H. B. Steward (New York: John Wiley and Sons, 1986); 14 pages.

* cited by examiner

*Primary Examiner* — Christopher Mahoney
(74) *Attorney, Agent, or Firm* — St. Onge Steward Johnston & Reens LLC

(57) ABSTRACT

An endoscopic system with at least one light source for generating at least partially coherent light, for exciting fluorescent light, with at least one light-conducting element, where the at least one light source and the at least one light-conducting element are positioned in a proximal supply unit. It is further provided with an optical radiance transmission link in an insertion part and with at least one fluorescence converter for conversion into white light. According to the invention, at least one actuator is present, which is coupled with at least one light-conducting element and/or with the at least one light source and/or with the at least one fluorescence converter. With the help of the actuator, perturbations or fluctuations concerning the at least one light-conducting element and/or the at least one light source and/or the at least one fluorescence converter are generated and thereby reduce the speckles in the endoscopic image.

19 Claims, 8 Drawing Sheets

SPECKLE REDUCTION OF MICROWHITE ENDOSCOPES

CROSS-REFERENCE TO RELATED APPLICATIONS

The present application claims priority of German patent application No. 10 2009 017 940.2 filed on Apr. 17, 2009, the content of which is incorporated herein by reference.

FIELD OF THE INVENTION

The invention relates to an endoscopic or microscopic system for illuminating a surgical area.

BACKGROUND OF THE INVENTION

An endoscopic system of this type is known from patent application JP-2005-205195.

Endoscopes and microscopes constitute in medicine, by now, an indispensable aid for certain diagnostic and therapeutic questions. In particular, in the context of minimally invasive surgery they make possible a mild alternative to conventional open surgery. The brightest possible illumination of the examination area is an urgent necessity in exploring the examination area, which normally is completely dark, with the help of the observation system of an endoscope, which can take the form of a classical relay-lens system, a fiber image conductor, or an electronic image sensor chip (CMOS, CCD) for video image reception In addition to their use in human or veterinary medicine, endoscopic or microscopic examinations have proven themselves as well in technical areas, such as for examining hollow cavities in turbines and engines. Even in these applications, good illumination of the area of investigation can be indispensable for an accurate depiction by the observation system of the endoscope, and should also provide a quantitative measure of fissure lengths.

The examination area is normally illuminated by a light conductor with a small cross-section, consisting of an optic fiber or a fiber bundle by which light is conducted from an external light source into the examination area.

The light source must therefore convey light with a high capacity or capacity density, in order to ensure sufficient illumination of the hollow areas.

For this purpose, arc lamps such as high-pressure xenon short-arc lamps are generally used. These arc lamps radiate incoherent light, which in some cases is imaged or focused onto the light entry end of the optic fibers or of the fiber bundle by means of an appropriate diaphragm or lens system.

Increasingly, however, light diodes and lasers, in particular laser diodes (LD), are coming into use. Laser diodes comprise higher light densities than light arc lamps. Laser light sources, in addition, have a long lifetime. Laser light can be easily transmitted by thin probes and cables.

Among possible laser light sources for endoscopes and OP microscopes are laser-pumped fluorescent light sources, continually modulated or pulsed (IR) lasers, blue or UV lasers for fluorescent excitation, continually modulated or pulsed blue or UV lasers, RGB/RGBA white light laser light sources, supercontinuum white light laser sources, or IR lasers.

The light that is usually emitted by a laser comprises narrow spectral bands. Because of this spectral purity, laser light can preferably be used, in particular, for fluorescent excitations, because this makes it easy to filter out the excitation light. For color reproduction, however, it is optimal to use a white illuminating light with a spectral characteristic as close as possible to a black body radiance.

In patent application JP 2005-205195, therefore, a fluorescence converter is positioned in the illuminating beam path to generate white light, on the additive color mixing principle, from the blue excitation light of a laser and the yellow light portions arising in a fluorescence converter. The light radiated from an LED or a laser diode (LD) in the blue spectral range is fed by a condenser device into a thin multimode glass fiber. The other end of the glass fiber is equipped with a wavelength transformer element. This element consists of an output portion on the end of the glass fiber, which is encased with fluorescent material. Because of the white light generation concentrated on the distal end of the glass fiber, the embodiment is especially suited for endoscopic applications. By selecting the laser emission wavelengths and the composition of the fluorescent material, a range of color shades is possible in the fluorescence conversion and color mixing.

The radiated light from lasers is coherent because of the process of its production, whereas the fluorescent light emitted by the fluorescent body because of the excitation with laser light is incoherent.

The fluorescence converter is also called a fluorescent body in order to emphasize its property as a diffuser body that diffuses the passed-through excitation light in all spatial directions. The diffusion occurs because of the diffuser centers mounted in the volume of the fluorescent body and because of structural effects on the surface. Here the diffuser centers can at the same time also be fluorophores. Because of their dimensions, the diffuser centers selectively can preferably diffuse the short wavelengths.

Because of the illumination of a surface with at least partial coherent light, so-called speckle patterns can develop on the illuminated area, which can be seen in images of the illuminated area taken with a video camera.

The speckles are frequently characterized by a granular, bumpy or sandpaper-type texture. The appearance of a speckle can resemble a surface that is sprinkled with fine particles.

The formation of speckles is less conspicuous and disturbing with moveable, hand-held endoscopic instruments than with stationary instruments or systems, for instance an operation microscope. Because of the stationary, immobile position of the operation microscope or of the target object, the speckles are not transmitted temporally by any hand-shaking motion (tremor) and thus are substantially more recognizable. Thus, also with OP microscopes in addition to the aforementioned endoscopes, a reduction of the speckles is very important.

U.S. Pat. No. 4,011,403A discloses a laser-illumination and observation system in which means are available for periodic excitation of the system for purposes of speckles reduction.

Reducing the speckle pattern is indispensable for a reliable evaluation of the image information. Thus, for instance in industrial applications like the inspection of hollow engine spaces, the apparently rough texture of the speckle artifacts can be mistaken for corrosion, impurities, or deposits.

In medical applications, confusion of the speckle pattern with the appearance of lesions, for instance, could lead to misdiagnoses in medical examinations.

It is consequently the task of this invention to further develop an endoscopic or microscopic system of the aforementioned type so that it efficiently provides an illumination of the examination area that is as free as possible of speckles.

SUMMARY OF THE INVENTION

With respect to the aforementioned endoscopic or microscopic system, the task is solved in that an aperiodic disturbance of the at least one light-conducting element and/or of the at least one light source by means of an actuator is used to achieve the most effective and efficient possible reduction of speckles.

The term "disturbance" in the context of the invention encompasses the aperiodic, chaotic, and stochastic use of a physical magnitude as well as modifications in a physical magnitude that include otherwise random components in their time span. The term "disturbance" is to be understood as including in particular mechanical motions, deflections, vibrations, oscillations, or trembling motions. The mechanical motions can include aperiodic, chaotic, irregular, unforeseeable time sequences or those involving other accidental components. The time sequence of a mechanical motion can also be composed of aperiodic, recurring portion and of a portion that is aperiodic, chaotic, irregular, unforeseeable, or involving other accidental components, and consequently can be aperiodic as a whole. As a result, according to the invention a disturbance is produced having a broad range of frequency and amplitude excitation, leading to a highly efficient reduction of speckles.

The disturbances can cause a modification of the index of refraction of the propagation medium in which the light is transported. With mechanical vibrations, mechanical differences in tension arise, which cause modifications of the index of refraction. Consequently the phase of the light is modulated, so that its coherence can be reduced. In using a Pocker or Kerr cell, by applying tension to the electrodes of the cell an electrical field is produced that can lead to a modification of the index of refraction. As a result of these modifications of the index of refraction of the propagation medium, in turn, the phase of the coherent light can be modulated and its coherence can be reduced. The reduced coherence allows a temporal alignment of the speckles, so that their occurrence and intensity are reduced.

The term "actuator" in the context of the invention refers to a converter that converts electrical signals, for instance, into mechanic motion. Actors can directly influence physical magnitudes such as temperature, pressure and density of gasses, position and motion of bodies in space. They can also cause electromagnetic effects such as, for instance, electromagnetic waves and impulses.

Actors can also include, for instance, electrical motors, electrodynamic converters, and electrostrictive, magnetostrictive, or piezoelectric actuators, in particular low volt piezo actuators. Preferred electrical motors include vibration motors that are installed in mobile telephones to trigger the tactile alarm. Because of their economical size, they are ideally suited for use in an endoscopic system. In addition, mass production makes them cost-effective. Actors that influence electrical fields as physical magnitudes can be, for instance, the electrodes of a Pockel or Kerr cell.

The terms "light-conducting element" or "light conductor" according to the invention include all means known to specialists that can be applied for transmitting the light from the light source to the distal end of an endoscope or microscope. They include, for instance, optic fibers, single-mode fibers, multi-mode fibers, fiber bundles, light-conducting cables, lenses, rod lenses, pulses, filters, light conversion elements, light plugs, mirrors, fiber cones, glass cones, glass bodies, crystal bodies, light boxes, as well as light couplers for connecting the light-conducting fiber(s) to the light source.

The term "coupling" according to the invention designates every connection that ensures at least partial transmission of energy produced by the actuator. Coupling can be produced as a rigid connection, in particular as a material, form, or power locking connection with the help of a coupling element, allowing a permanent transmission of mechanical motion energy. Coupling can also take the form of a loose connection that exists only at times and causes no complete transmission of mechanical energy from the actuator. It can also be configured as a coil that picks up electromagnetic impulses and thus electromagnetic energy.

Light sources used according to the terms of this invention to produce at least partly coherent light can also include spectral portions of the UV or IR spectral range of the electromagnetic spectrum.

In a first embodiment of the invention, the light source and actuator are mounted together on a cooling body, which causes both the off-loading of the heat output of the light source as well as the transmission of the actuator's mechanical excitations to the light source. The cooling body applied elastically for this purpose thus also serves as a coupling element in addition to its original function. The actuator is thus provided with a control switch that feeds the actuator with a chaotic input signal. The actuator converts the electrical input signal into corresponding mechanical motions, which possess the time sequence of the chaotic input signal. The mechanical motions are transmitted by the cooling body to the light source and stimulate the latter to chaotic motions with low deflection around their resting position.

As a result of these measures, there is advantageously no longer a necessity for an additional component for coupling the actuator to the light source, thus saving material costs.

An additional advantage of positioning the actuator on the cooling body is that it becomes possible to carry out an exchange of the actuator and of the related control electronics in a manner that is especially simple and timesaving. Because the actuator and the control electronics are positioned on the cooling body to be freely accessible, no additional time is required during repairs for removing or installing the cooling body.

In an additional preferred embodiment the actuator is connected directly with a light-conducting element. For this purpose the actuator can include, for instance, a linear power drive or a crank mechanism with drive rod, having a hole-like aperture, for instance as a bore-hole, perpendicular to the drive direction, through which a light-conducting fiber or a fiber bundle as a light-conducting element can be form-locked or loosely fed in.

As a result of this measure, it is possible to avoid disadjustment of the light source, its imaging lens, as well as other imaging optic components within the endoscopic or microscopic system because of mechanical disturbances caused by the actuator in the endoscopic or microscopic system.

In a preferred embodiment, a coupling element that can be excited to rotating motions connects the actuator with the light conductor.

This measure can advantageously be achieved easily, because a coupling that can be excited to rotating motions in the form of an Unruh is a mass-produced item in the watch industry and thus can be obtained easily and cost-effectively. In addition, Unruhs and their actuators are available in miniaturized form thanks to the steady developments of the watch industry, and are adjusted to the requirements of space reduction for use in an endoscope or microscope.

In another preferred embodiment, the coupling element comprises an attenuator.

This measure has the advantage that the excitation energy transmitted by the coupling element can be limited in its effect in order to avoid unintended reinforcement of disturbances in the endoscopic or microscopic system, such as in the form of a resonance catastrophe.

In another preferred embodiment, the actuator comprises an imbalance.

As an advantageous result of this measure, it is possible to dispense with a separate control switch, which for instance causes a chaotic input signal for the actuator. Instead, the actuator can be operated with a customary direct or alternating current. The actuator produces aperiodic modulated excitation energy, which because of its property converts the light element into a chaotic mechanical motion. Consequently this avoids the cost and complexity for an electronic control switch, which produces a random component. The random component, which is transmitted as a disturbance to the endoscopic or microscopic system, arises because of the mechanical configuration of the coupling. It requires no control function that includes a random component. Because of the random component, in addition there arises a disturbance with a broad frequency and amplitude range, which advantageously allows an efficient reduction of speckles.

The actuator can advantageously be configured as a cooling ventilator with imbalance, so that the imbalance of the cooling ventilator is produced by localized weighting or removal of part of one blade of the cooling ventilator, especially by break-off.

As a result of this measure, a cost-effective, easily constructed, and replaceable actuator is made available with imbalance as a compact component.

In an especially preferred embodiment, by means of the coupling a loose connection is produced between actuator and light conductor. A belt, ring, noose, eyelet, drive rod with borehole, or a screw-shaped curved wire, for instance, can serve as coupling element. The light conductor is guided through the aperture in the coupling element. The light conductor can move freely in lateral direction inside the space surrounded by the edges of the coupling element. The actuator executes mechanical motions, for instance, whose deflections are greater than or equal to the maximum diameter of the cross-section of the aperture of the coupling element. The light conductor also experiences a force, such as a blow, upon the deflection of the coupling element by the actuator, if the distance from the light conductor to the edges of the aperture is smaller than the deflection of the coupling element. Relatively small deflections, for instance, then cause an excitation blow if the light conductor touches the coupling element or is pressed against the light conductor with an insignificantly small force. Because the relative position between the light conductor and the edges of the aperture of the coupling element continually changes in unforeseeable manner, the light conductor experiences a series of blows of purely random character. To produce a random excitation blow requires no control that would contain a random component. Another advantage of this configuration of the coupling is that it can be produced particularly cost-effectively and simply and in addition allows an aperiodic disturbance.

In an additional embodiment the light source, the optic light element, and the actuator are positioned in the proximal supply unit.

This measure has the advantage that the endoscopic or microscopic system comprises a compact structure that is technically simple to produce. In addition, this embodiment of the endoscopic or microscopic system proves to be advantageous during the operation because the endoscopic or microscopic system comprises only the housing portion of the proximal supply unit, rather than consisting of several housing parts, so that when the endoscopic or microscopic system is set in motion, for instance, no difficulties can arise that would result from a structure with several housing parts.

In an additional preferred embodiment, the optic conductor element is configured so that it is electrically and/or thermally insulating.

This measure has the advantage that no flow of current can be conducted from the light source that is electrically charged to the optic light-conducting element, that is to the light-conducting cable and housing. This increases the safety for the person using the endoscopic or microscopic system, for instance during a medical examination. In addition, the light-conducting element cannot heat up from the inflowing current, so that is not adversely affected by heat in its functioning.

In another preferred embodiment, the optic light-conducting element is configured as a glass body, in particular as a lens.

This measure makes possible, advantageously, an embodiment of the optic light-conducting element that is sufficiently known from the state of the art in order to collect light emitted by the light source and, in some cases, to couple it in additional light-conducting elements such as fiber cones, glass cones, light-conducting fibers, and light-conducting cables. In addition, a glass body is especially cheap to produce and because of its low electrical conducting capacity ensures an electrical insulation between the light source and the light-conducting cable. The light-conducting element can also be configured, for instance, as a compound elliptical concentrator (CED) or as a compound hyperbolic concentrator (CHC).

In an additional alternative embodiment, the optic light-conducting element is made of optic light-conducting fibers.

This measure likewise offers an advantageous configuration of the optic light-conducting element. The use of light-conducting fibers avoids costly surface shape of the glass body for light-conducting, because the light rays emitted by the light source are conducted by the alignment of the optic light-conducting fibers by the optic light-conducting element. In addition the use of light-conducting fibers allows the exploitation of the entire surface of the distal end area of the light-conducting element that faces the front side of a possibly adjoining positioned light-conducting cable, in order to couple the light rays into the light-conducting cable.

In another preferred embodiment, the optic light-conducting element tapers in the direction of the light source.

This measure has the advantage that the cross-section surface of the first end area of the optic light-conducting element can be optimally adjusted to the cross-section surface of the light source or of the fluorescence converter, and consequently an efficient coupling of the light into the optic light-conducting element becomes possible. In addition, the light rays in the optic light-conducting element are widened because of its configuration that widens toward a possibly adjoining light-conducting element, so that the front side of the possibly adjoining light-conducting element, which comprises a greater diameter than the active surface of the light source or of the fluorescence converter, is optimally illuminated.

In another preferred embodiment, the at least one coherent light source is configured as a semiconducting laser, in particular a diode laser.

This measure has the advantage that with the development of constantly more economical and higher-capacity diode lasers, they can be used as efficient light sources in the field of endoscopy or microscopy.

In another preferred embodiment, the light source includes several diode lasers, which emit light of varying wavelength in various ranges of the electromagnetic spectrum, in particular in the visible range.

This measure has the advantage that the coupling of laser light of various wavelengths makes possible a spectral adjustment to the requirements for observing the scenery in the examination area.

In another preferred embodiment, a fluorescence converter is positioned on the distal end of the insertion part and is excited to oscillations, according to the invention, by means of an actuator to reduce speckles.

This measure has the advantage that the effect of the fluorescence converter can be exploited in advantageous manner as a diffuser body. Emitted fluorescent light from the fluorescence converter is sent out in every direction. In addition the fluorescence converter is appropriate as a diffuser body for the at least partially coherent light of the at least one light source and can diffuse this light in all directions. Consequently it is possible to achieve a more uniform illumination of hollow cavities.

In another preferred embodiment, the fluorescence converter is positioned in the proximal supply unit.

This measure has the advantage that, as a result, a good cooling of the fluorescence converter can be achieved in the proximal supply unit that can be used as a separate illuminating unit. Because of this modular structure, the proximal supply unit can also be used with various insertion parts, thereby increasing flexibility in the assembly and structure of an endoscopic or microscopic system.

In another preferred embodiment, the actuator is configured as a vibration motor, which is usually employed to trigger the tactile alarm in mobile telephones.

This measure has the advantage that such vibration motors are economically available.

In another preferred embodiment, the actuator is an electromechanical converter, as is used for powering an Unruh in a watch.

This measure has the advantage that electromechanical converters used in the watch industry have a miniaturized structure, which is particularly suited for insertion in the proximal operating part, for instance of an endoscope, because of the necessity of compressed size.

In another preferred embodiment, the actuator is a ventilator.

This measure has the advantage that, in addition to mechanical excitations that are coupled by the ventilator and can be used to produce disturbances in the endoscopic or microscopic system, the system's airflow can also be used to cool the light source.

In another preferred embodiment, the actuator is a customary commercial speaker with an upstream-mounted frequency generator.

This measure has the advantage that speakers can be purchased economically and easily built into a housing. Signals with frequencies greater for instance than 20 kHz can be produced by the upstream-mounted frequency generator. These frequencies cannot be perceived by the human ear. The speaker is fed with signals having frequencies greater than 20 kHz. Consequently the membrane of the speaker excited to oscillations with frequencies that are substantially greater than 20 kHz.

In an alternative embodiment, the speaker is excited at lower frequencies in the 10 to 1000 Hz range. As a result, a greater oscillation amplitude can be produced with substantially greater power, so that improved alignment and thus reduction of the speckles can be achieved.

An especially advantageous embodiment of the speaker is possible if the speaker is open.

With an open configuration of the speaker, the pressure waves produced on the front side of the speaker membrane are essentially compensated by counterpressure of the membrane rear side. As a result, at low frequencies, such as frequencies that are below or equal to the quotient of the speed of sound and speaker diameter, sound is emitted that is scarcely audible. Thus the emission of sound disturbances is favorably reduced, which contributes to keeping the impact of ambient noise at low levels.

With the open construction of the speaker, pressure waves produced on the front side of the speaker membrane are essentially compensated by counterpressure on the membrane rear side. Consequently, scarcely audible sound is emitted at low frequencies, that is, those below or equal to the quotient of the speed of sound and speaker diameter. Thus, the emission of disturbance noise is minimized in favorable manner, contributing to keeping the impact of ambient noise low.

In an additional preferred embodiment, the proximal supply unit of the endoscopic system comprises an electrically insulating holder element in which the optic light-conducting element is positioned.

This measure advantageously allows additional insulation of the light source that is impacted with tension from the optic light-conducting element and housing of the proximal supply unit, so that risk to persons is likewise reduced.

In another preferred embodiment, the proximal supply unit of the endoscopic or microscopic system comprises an electrically insulating and noise dampening holder element in which the actuator is positioned.

This measure advantageously allows a minimization of the mechanical disturbances that can be transmitted unintentionally to other parts of the endoscopic or microscopic system than the light-conducting element that is to be excited. In addition, because of this measure it is possible to produce a sound damping of the undesired incidental noises that can arise upon operating the actuator.

In another preferred embodiment, the proximal supply unit of the endoscopic or microscopic system comprises a low-friction holder element in which the coupling element is positioned.

Because of this measure, the greatest possible loss-free transmission of energy from the actuator to the light-conducting element is advantageously achieved.

Additional advantages or properties can be seen from the following description and the appended illustrations. It is understood that the aforementioned properties, and those yet to be elucidated, can be applied not just in the specifically indicated combination but also in other combinations or in isolation without departing from the context of the present invention.

Embodiments of the invention are depicted in the illustrations and are disclosed in greater detail in the following parts of the patent description.

DETAILED DESCRIPTION OF THE INVENTION

Figure 1:
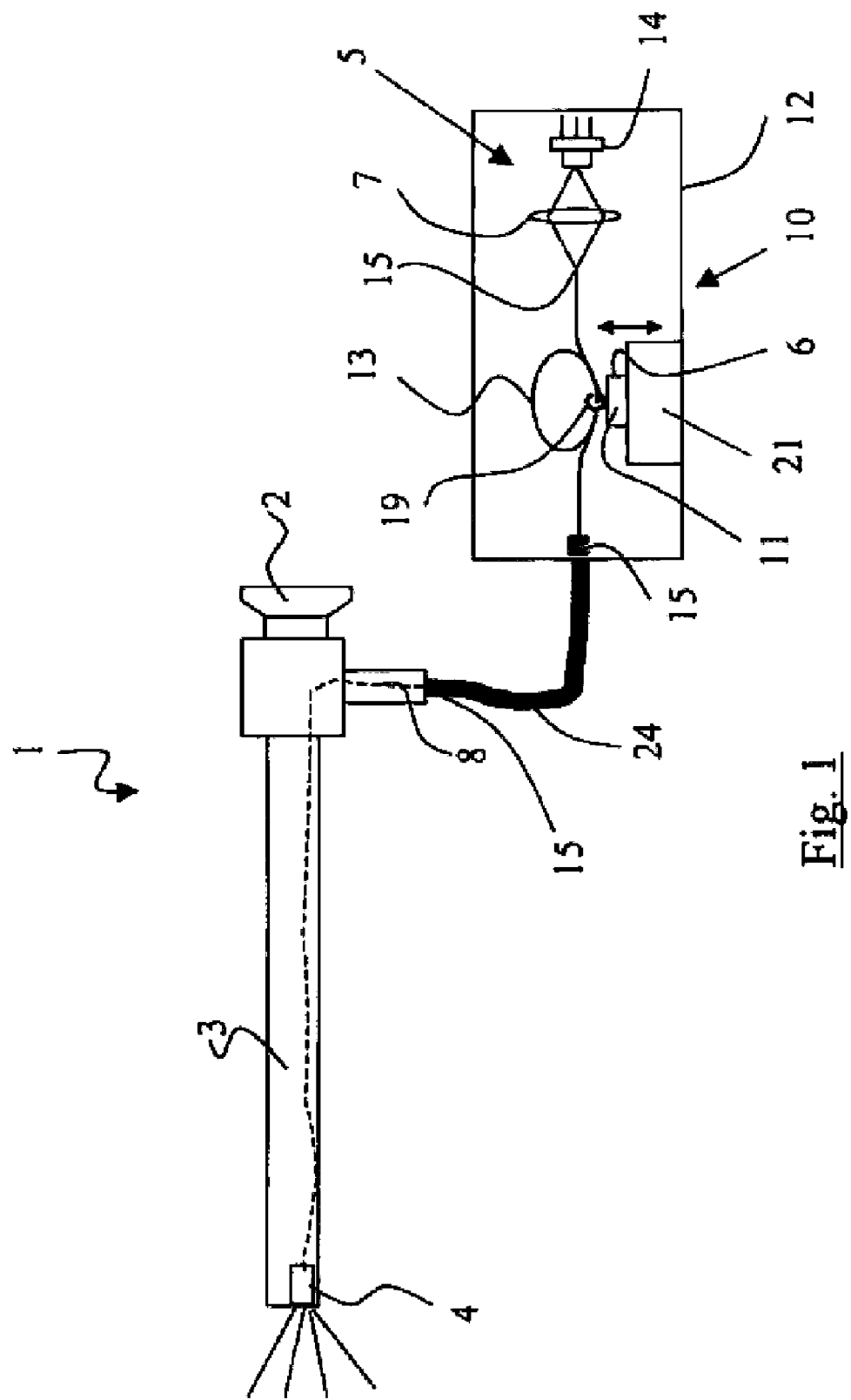
FIG. 1 shows a schematic depiction of an endoscopic system.

FIG. 1 shows schematically an endoscopic system 1 with eyepiece 2 and insertion part 3. The insertion part 3 can be configured as a rigid tube or flexibly. Ahead of or instead of the eyepiece with optic transmission of the observed image, a video camera can be provided with the observed image depicted on a monitor. Mounted in a supply unit 10 is an excitation beam source 5, which contains a laser diode 14 and a coupling lens 7 for feeding the excitation light into a light conductor 13, which is configured as a glass fiber. The coupling of the excitation light can also occur directly without insertion of a coupling lens by quasi-contacting the surface of the chip of the laser diode with the proximal end of the glass fiber 13, where if necessary a minimum distance to the output mirror of the laser chip must be guaranteed for sufficient recoupling into the laser medium. It is also possible of course to provide additional laser diodes with emission of additional wavelengths, whose radiance can likewise be fed into the light conductor 13 or into additional glass fibers. Thus, for instance, spectral weaknesses of the white light can be compensated. The laser diodes can be battery-operated or provided with energy by a network part.

The glass fiber 13 is passed through a coupling element 19 configured as a metallic eyelet. The metallic eyelet 19 is soldered onto the housing 6 of the actuator 11, which is configured as vibration motor. The vibration motor 11 is positioned on a holder element 21, which is secured on the housing 12 of the supply unit 10. The holder element 21 is at least partly made of materials that possess high elasticity and/or a high damping effect. Through a corresponding appropriate selection of material components of the holder element 21, it is possible to reduce any transmission of mechanic motions, caused by the vibration motor 11, onto the housing 12 of the supply unit 10. The holder element 21 exerts an effect that is comparable to a shock absorber in automotive technology. The eyelet 19 is struck against the glass fiber 13 by means of the motions of the vibration motor 11. The reserve length of the glass fiber 13 can be formed into a spiral. This allows a great part of the glass fiber 13 to be excited to mechanical motions, without at the same time necessarily raising the amplitudes of the vibration motions of the vibration motor 11. In FIG. 1 the double arrow indicates the direction of motions caused by the actuator 11 in the illustrated embodiment.

To connect the supply unit 10 with the endoscopic system 1, a light-conducting cable 24 is provided, which can be connected to the supply unit 10 by special or commercially produced plug-in connection on the endoscope or for instance with a light-conducting plug 15. Other types of connection are also possible, such as demonstrated in the detail in FIG. 2. The plug-in connections can, in particular, be produced as autoclavable and laser-protected. The glass fiber 8 is usually fed through the insertion part 3 to the distal end, either loose or in a separate illumination channel or in a protective casing. At the distal end a fluorescence converter 4 is positioned, in which the conversion occurs in white light. The fluorescence converter 4 can be functionally replaceable or integrated into a replaceable exchange head on the distal end of the insertion part. The imaging lens is not further illustrated here.

Figure 2:
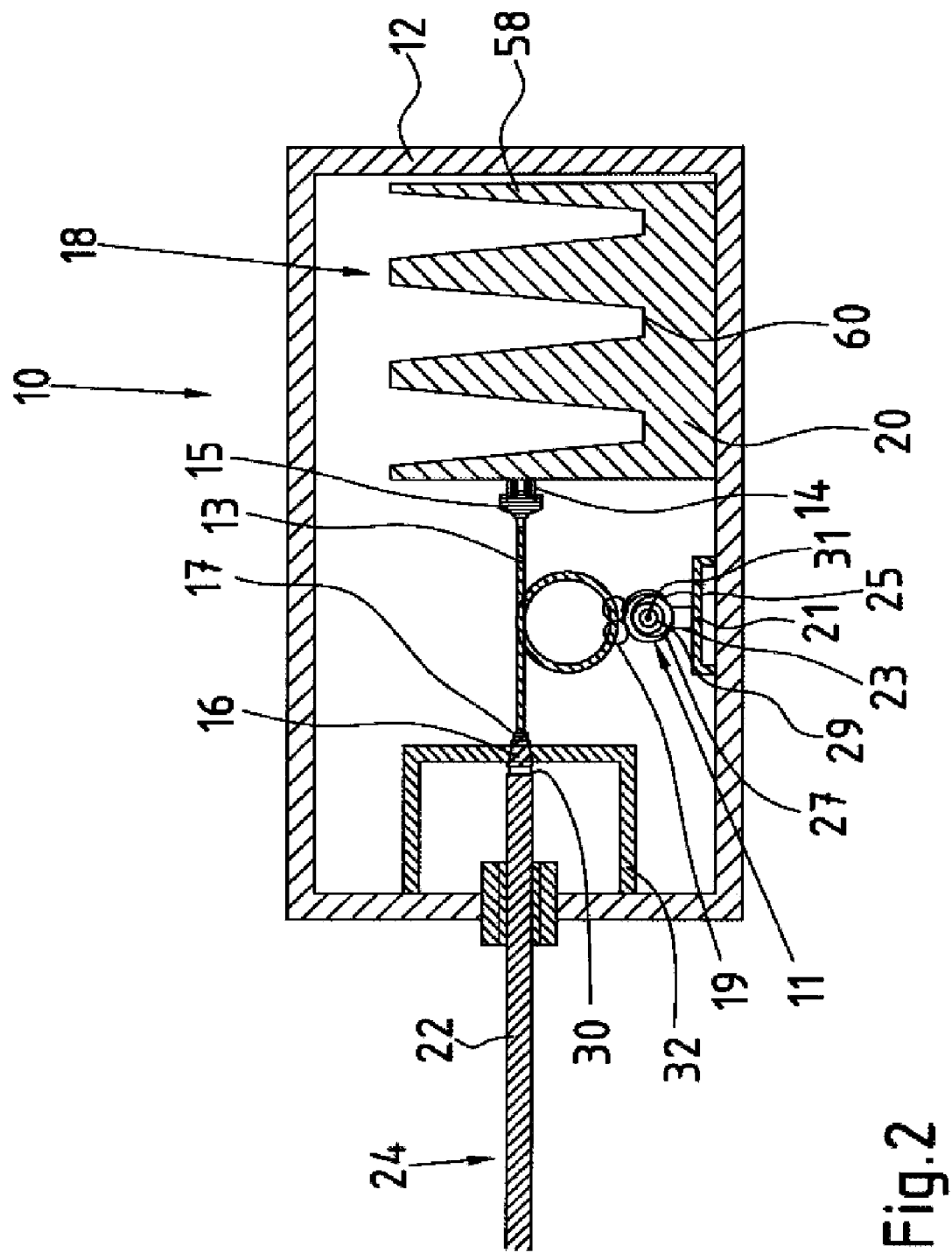
FIG. 2 shows a schematic depiction of the proximal supply unit of FIG. 1.

The supply unit 10 of the endoscopic system 1 is shown in FIG. 2. The supply unit 10 comprises a housing 12 in which a light source 14, a light conductor 13, an actuator 11, coupling element 19, and a cooling device 18 are positioned.

The light source 14 is thermally conducting in connection with the cooling device 18; that is, with a heat conductible cooling body 20, where a thermally conducting connection is understood as a direct or indirect thermal coupling of both components. The cooling body 20 is positioned on a side of the light source 14 turned away from the optic light conductor 13, where the light source 14 is mounted preferably directly on the cooling body 20, so that heat produced by the light source 14 can be given off directly to the cooling body 20 and removed by it. The cooling body 20, in addition, is thermally conducting in connection with the housing 12, so that heat absorbed by the cooling body can be diverted to the housing 12. The cooling body 20 in terms of its dimensions is configured to be large in comparison to the light source 14, so that the cooling body 20 can efficiently absorb and remove heat produced by the light source 14.

The actuator 11 sits on an elastic carrier element 23 that is secured onto a holder element 21. The holder element is directly connected with the housing 12. A motor 27 with an imbalance element 29 is positioned in the housing 25 of the actuator 11. When the motor 27 is in operation, the imbalance element, configured in the form of an eccentric disc, rotates around the motor shaft 31. The housing 25 of the actuator 21 is deflected by the rotary motion of the imbalance element. These deflections are transmitted directly onto the coupling elements 19, which are in material connection with the housing 25. The elastic carrier element 23 prevents transmission of the deflections onto the holder element 21, whereby the deflections could spread themselves to the housing 12 and thus in the entire supply unit and would lead to unintended disturbances of the endoscopic system 1.

The light-conducting element 11 is configured as light-conducting fiber. It is in a light-conducting connection by a light-conducting connector 15 with the light source 14, which is configured in the form of a diode laser. The light-conducting element 13 is conducted through by the larger openings of the coupling elements 19, which are configured in the form of metal rings. The coupling elements 19, when the motor 27 is in operation, strike from time to time unforeseeably against the light-conducting element 13 because the eccentric disc 29, which rotates around the motor axis 31, deflects the housing 25 of the actuator 11 and the coupling elements mounted on it. As a result, the course of the beam path is modified in the light-conducting fiber, so that the coherence of the light of the laser diode 14 on the distal transition of the light fiber 13 to the optic light-conducting coupling element 17 is destroyed. The light-conducting coupling element 17 produces a light-conducting connection between the light-conducting fiber 13 and the optic light-conducting element 16.

A proximal end 22 of a light-conducting cable 24, which is connected with an insertion part (compare FIG. 1), can be inserted into the housing 12 through a cylinder 28 mounted in an aperture 26 of the housing 12, or the proximal end 22 of the light-conducting cable 24 can be mounted, once inserted, firmly in the supply unit 10. The proximal end 22 of the light-conducting cable 24 comes to rest in the housing 12 in such a way that a front surface 30 of the proximal end 22 of the light-conducting cable 24 points in the direction of the light source 14 and is positioned at a close distance from it. Mounted between the front surface 30 of the proximal end 22 of the light-conducting cable 24 and the light source 24 is the electrically insulating optic light-conducting element 16, which is held by an electrically insulating holder element 32 in the housing 12.

Figure 3:
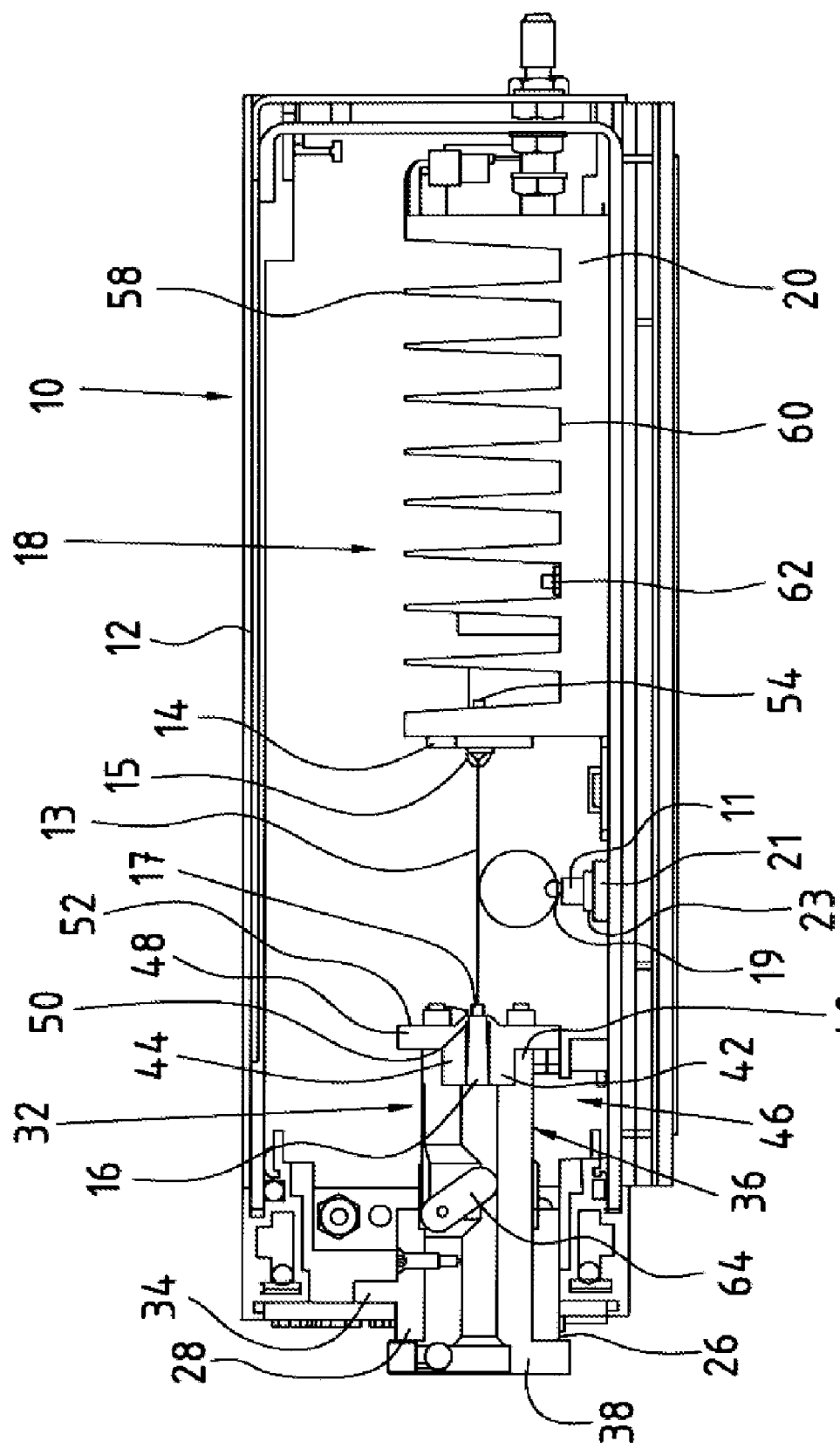
FIG. 3 shows a detailed depiction of the proximal supply unit of FIG. 1.

According to FIG. 3, the cylinder 28 is positioned in the opening 26 in order to insert the proximal end 22 of the light-conducting cable 25 into the housing 12 of the supply unit 10. The cylinder 28 is configured as a short, cylindrical hollow tube with a ring-shaped widening 34 that serves to secure the cylinder 28 on the housing 12. Mounted in material connection in the cylinder 28 is a frame 36, which likewise is configured as a cylindrical hollow tube. A first end area 38 of the frame 36, which is positioned outside the cylinder 28, that is, outside the housing 12 and is inserted through the proximal end 22 of the light-conducting cable 24 into the housing 12, is widened in a ring shape. A second end area 40 of the frame 36 comprises a fully surrounding recess 42, whose diameter is greater than an interior diameter of the frame 36. A first segment 44 of a disc 46 is enclosed, in material connection, in the recess 42. A second ring-shaped segment 48 of the disc 46 comprises a greater outer diameter than the first segment 44 of the disc 46 and than the frame 36, so that it extends beyond the frame 36. The disc 46 also comprises a cylindrical passage 50 whose inner diameter corresponds approximately to an inner diameter of the frame 36. The optic light-conducting element 16 is mounted in the passage 50 of the disc 46.

The holder element 32 shown in FIG. 2 is configured here as the frame 36 and the disc 46, where both components are produced from an electrically insulating material such as plastic.

The light source 14 is positioned at a distance from the a front side 52 of the second segment of the disc 46 and connected backwards with the cooling body 20 by at least one screw 54, where the at least one screw 54 can be configured, for instance, as an M3 thread.

A light-conducting fiber 13 is in a light-conducting connection with the light source 14 by way of a light-conducting plug connector 15. The distal end of the light-conducting fiber 13 is in light-conducting connection with the optic light-conducting element 16, which is positioned in the cylindrical passage 50, by means of a light-conducting coupling element 17.

The light-conducting fiber 13 is surrounded by the coupling element 19, which is configured for instance as a metallic ring. In the embodiment of FIG. 2, no material or form-locking connection exists between the coupling element 19 and the light-conducting fiber 13.

The coupling element 19 is in material connection with the actuator 11, which takes the form of a vibration motor in the embodiment illustrated in FIG. 2, as it is used for tactile signaling in mobile telephones. The actuator 11 is connected, by non-illustrated connecting connections, with a control can be operated by a switch and regulator on the front side (not illustrated) of the supply unit 10. The actuator 11 in particular can be switched on and off, so that more complex switchings of the powering of the actuator 11 can also be arranged.

The actuator 11 is positioned on an elastic carrier element 23, which is mounted on a holder element 21 that is secured on the inside of the housing 12 of the illumination system 10. The elastic carrier element is configured in such a way that as few vibrations as possible of the actuator 11 are transmitted to the housing 12.

The cooling device 18 is configured as a passive cooling in this preferred embodiment and functions by heat conduction between the light source 14 and the cooling body 20. It comprises the heat conducting cooler body 20 that serves for conducting heat produced by the light source 14 and is positioned on the side of the light source 14 turned away from the optic light-conducting element 13. The cooling body 20 also comprises raised ribs 58 to increase heat deflection, which taper toward their free ends. The ribs are spaced apart in such a way that screws 62 are positioned in the intervening surfaces 60 and serve to secure the cooling body 20 to the housing 12.

Heat produced by the light source 14 is transferred to the cooling body 20 by the direct contact between the light source 14 and the cooling body 20 as well as by the at least one screw 54. Heat conducted to the cooling body 20 is distributed along the cooling body 20 and is conducted by it onto the housing 12.

The cooling device 18 can likewise be configured as a heat pipe, where the cooling body 20 is configured for this purpose, for instance as a closed-off hollow body of a heat-conducting material such as aluminum. A capillary-acting, wick-like material is positioned on an inside surface of the hollow body. The hollow body is also filled with a liquid under its own pressure or possibly under a reduced pressure. If heat is conveyed from the light source 14 to a surface of the heat pipe, then the liquid in the interior of the heat pipe starts to boil and converts to steam by absorbing heat energy. This steam is distributed in the hollow body and condensed while emitting heat to a cooler place on the inner wall of the heat pipe. The capillary acting, wick-type material again absorbs the condensed liquid and transports it back to a place on the heat pipe on which heat is conveyed. The heat pipe therefore forms a closed cooling circuit by which the illuminating system 10 can be cooled efficiently.

The proximal end 22 of the light-conducting cable 24 can be held in the frame 36 by a fixing mechanism. For this purpose a locking lever 64 is positioned on the frame 36, by means of which the proximal end 22 of the light-conducting cable, for instance, can be clamped shut.

Figure 4:
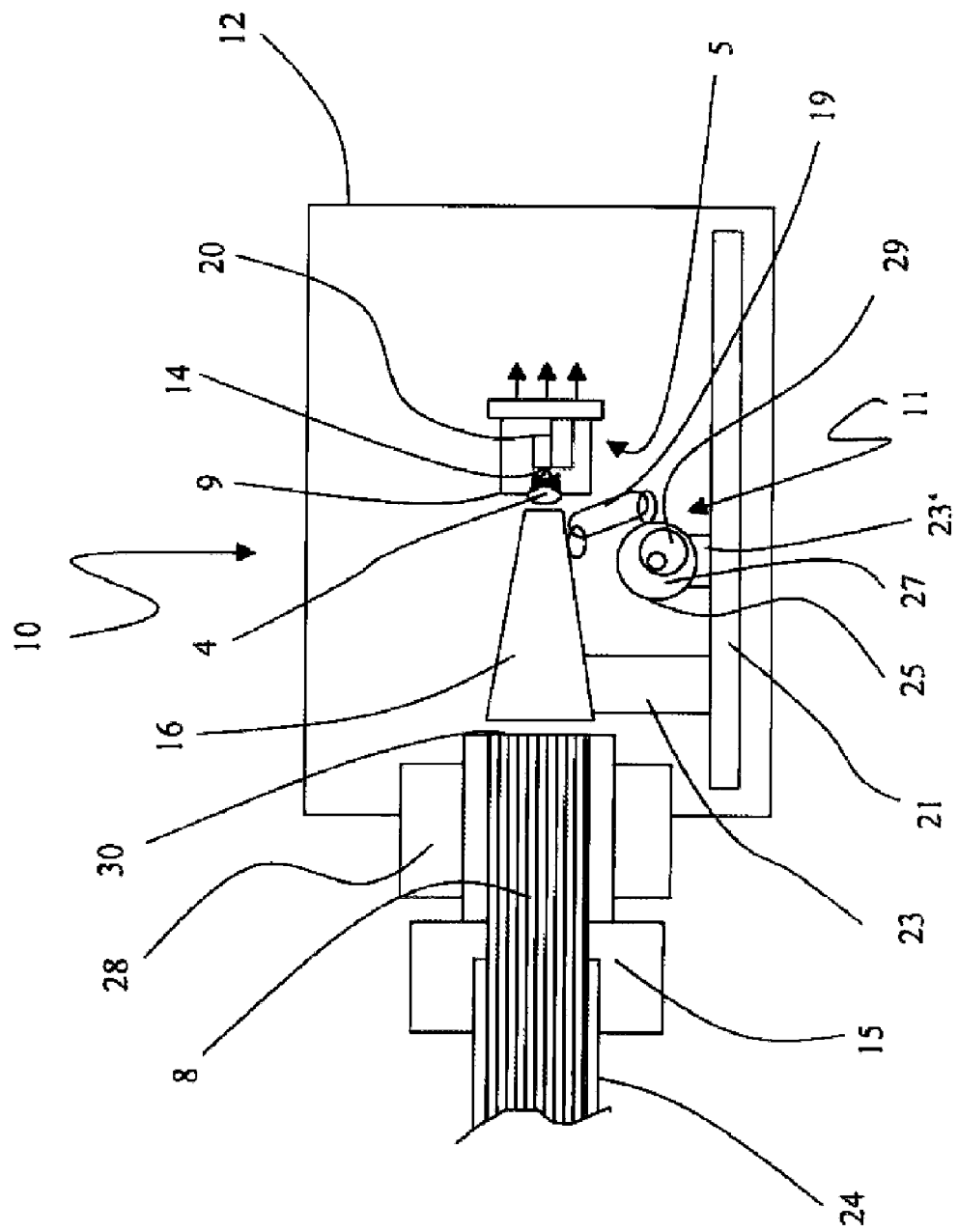
FIG. 4 shows a schematic depiction of a supply unit with proximally mounted fluorescence converter.

FIG. 4 shows a proximal supply unit 10 in which a fluorescence converter 4 is already positioned. The fluorescence converter 4 closes off the three-legged housing 9 of the excitation ray source 5. The light source 14 is configured as a laser chip whose active surface is turned toward the fluorescence converter 4 and illuminates said converter. The laser chip 14 is positioned on a cooling body or heat conducting body 20. The heat conducting body 20 is mounted on the housing 9. The heat is emitted from the laser chip 12 onto the heat conducting body 20 and then to the housing 9 and from there is conveyed onward to the supply unit 12 by cooling sheet metal that is not shown and by fixing elements.

The laser chip 14, which in this example supplies excitation light in the blue spectral range, excites the fluorescence converter 4. The fluorescent radiance of the fluorescence converter 4 and the transmitted excitation light of the laser chip 14 form a white light. This white illuminating light is radiated in a wide angle of the space (not shown) in the direction of the light-conducting element 16, which in this example takes the form of conical glass conical stump. Between the cover surface of the glass conical stump 16 and the fluorescence converter 4, compensating media, not illustrated, can be provided for flexible compensation of the index of refraction.

The glass conical stump 16 is secured on a socket-shaped elastic carrier element 23 made of rubber. The carrier element 23 is positioned on a holder element 21, which is installed in the housing 12 of the supply unit 10 in the form of a metal plate or circuit board. Situated beside it is an actuator 11. The motor 27 of the actuator 11 is mounted on an additional elastic carrier element 23'. The rotary motor 27 comprises an imbalance 29, which is secured on its motor axis.

The coupling element 19, which is formed from an open, three-member chain of ring-shaped links, is secured on the housing 25 of the motor 27 and on the glass conical stump 16. A connection for power transmission between the motor 27 and the glass conical stump 16 is thereby produced. The rotary motions of the motor 27, because of the imbalance 29, set the motor housing 25 in vibrations, which are transmitted by the individual chain members of the coupling element 19 onto the glass conical stump 16, so that the loose configuration of the transmission chain modifies the time sequence of the vibrations. The resulting disturbances cause tension modifications in the glass conical stump 16, which lead to corresponding time changes in the index of refraction of the glass conical stump. The oscillations of the index of refraction modulate the phase of the electromagnetic light, which is conducted by the glass conical stump 16. The temporal coherence of the excitation radiance is conveyed with the oscillations of the phase induced by the temporal variations of the index of refraction, so the index coherence is reduced and in the best case is realigned.

The front side 30 of a class fiber bundle 8 is positioned at a close distance essentially parallel to the ground surface of the glass conical stump 16. The intermediate space formed thereby can in turn comprise compensating media (not illustrated) for flexible compensation of the index of refraction in order to keep the light losses at this coupling site of the light conduction as low as possible. The glass fiber bundle 8 runs inside a light-conducting cable 25 whose distal end, not illustrated, is connected to the light-conducting connection of an endoscope. The light-conducting cable 24 includes on its proximal end 22 a plug-in connection 15, which is inserted form-locked into the connection cylinder 28 of the housing 12 of the supply unit 10.

Figure 5:
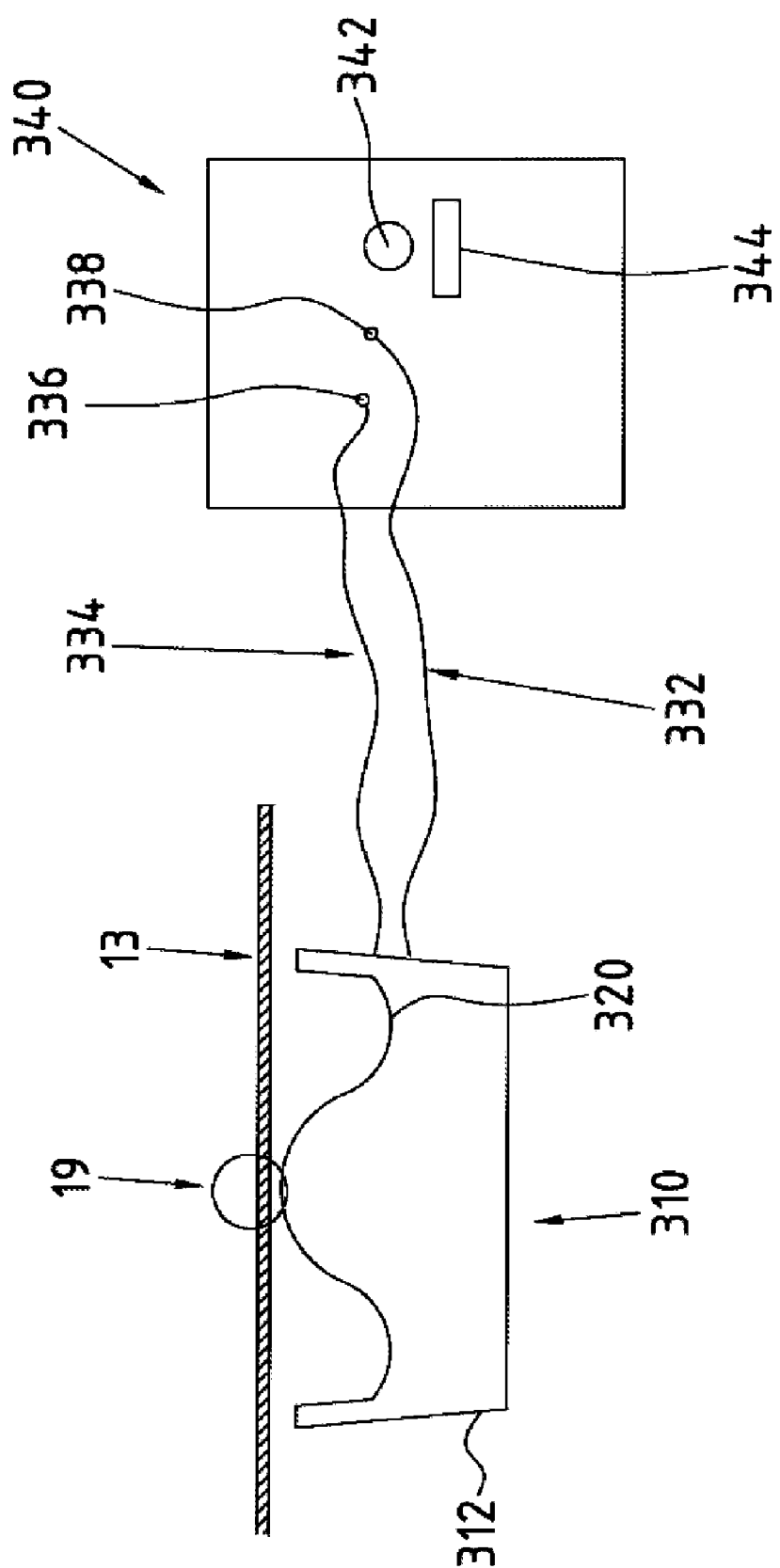
FIG. 5 shows an actuator with preferred coupling element and light-conducting element.

The actuator 11 can, as shown for example in FIG. 5, also take the form of a commercially available speaker 310. The speaker housing 312 is secured on the housing 12 of the illuminating system 10 (not shown). The coupling element 19 is cemented onto the speaker membrane 320 and is configured as a plastic ring. The light fiber 13 is conducted through the plastic ring 19 and is in light-conducting connection with the light source 14, which takes the form of a diode laser (not shown). The connecting lines 335 and 336 connect the speaker 310 with the frequency generator 340 by means of the connector cylinders 336 and 338. The frequency generator has available a regulator 342 and a frequency monitor 344. The speaker membrane can be impacted with signals of the frequency generator that can no longer be perceived by the human ear. These signals deflect the speaker membrane 320, which in turn deflects the cemented-on plastic ring 19, which pushes against the light-conducting fiber 13 and thus causes disturbances of the ray path in the light-conducting fiber 13.

Figure 6:
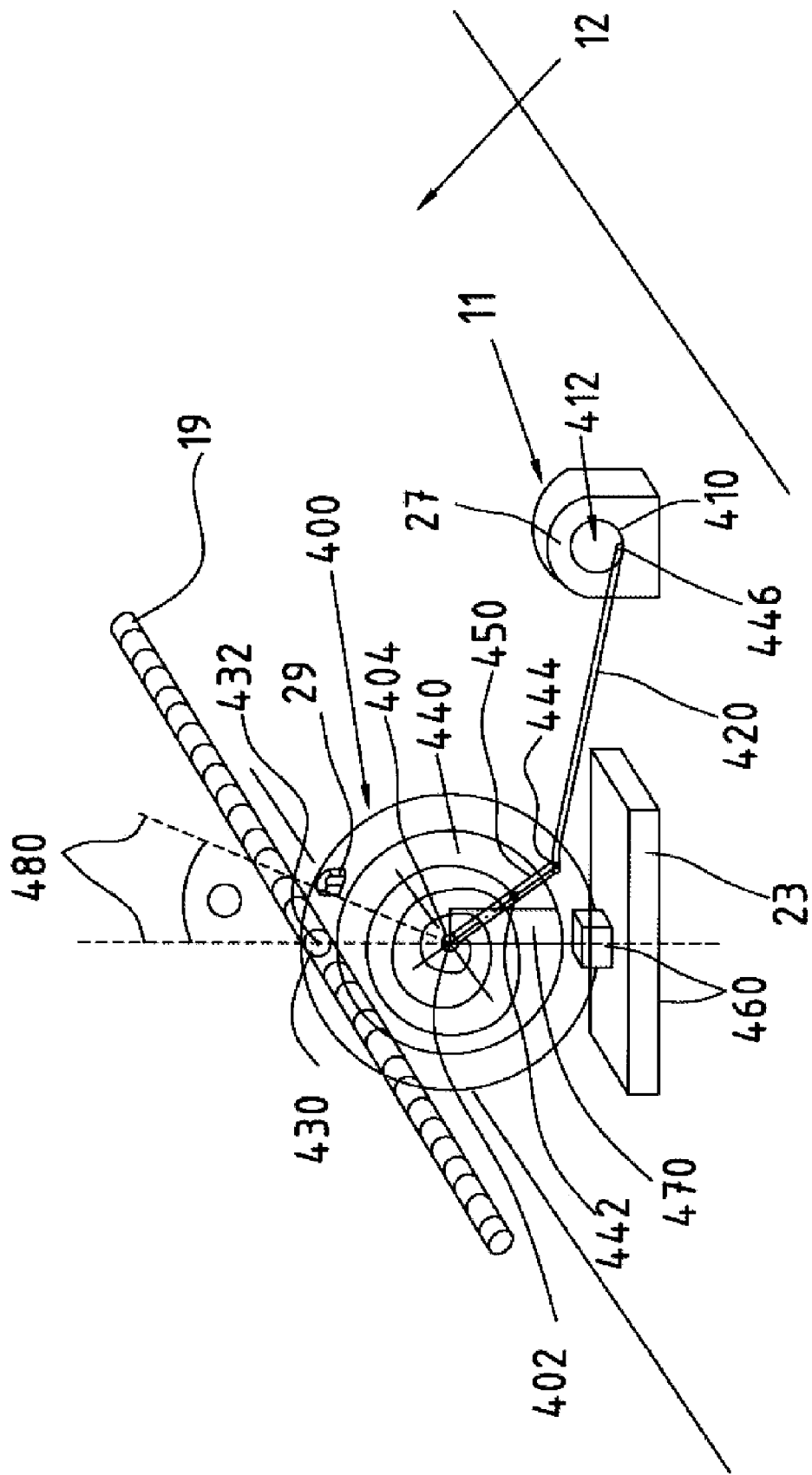
FIG. 6 shows another depiction of an actuator with coupling element and light-conducting element.

In the preferred embodiment shown in FIG. 6, a metallic flywheel 400 serves as coupling element between the actuator 11 and the light-conducting element 13. The flywheel is mounted rotatably on the axle 404 that is secured to the fixing rod 470. The fixing rod 470 is positioned on the elastic carrier element 23.

The flywheel 400 comprises, in addition to the central borehole 402 for the rotary axle 404 an outer axial borehole 430 through which the light conductor 13 is passed in form-locking connection. The light conductor 13 here can in addition be in a material connection with the flywheel, for instance by an appropriate cement or a molding mass that is inserted into the bore-hole 430 between the flywheel 400 and the light conductor 13.

The inner end of a spiral spring 440 is connected on the rotary axle 402 with the flywheel 400. The outer end of the spiral spring 440 engages in a borehole 442 of a lever 450, in which borehole the outer end of the spiral spring 440 is secured. The lever 440 is rotatably connected on the rotary axle 402 and rotatably connected with the drive rod 420 by a pin 444, which is surrounded by a borehole of the lever in form-locking connection.

The actuator 11 comprises an eccentric disc 410, which rotates around the rotary axle 412 of the motor 27. The drive rod 420 is form-locked through a borehole with the pin 446, which is secured on the eccentric disc 410. The rotary motion of the eccentric disc, which is set off by the motor 27, is transformed into a rotary motion of the flywheel 400 by means of the transmission chain, which is made up of the drive rod 420, the lever 450, and the spiral spring 440.

A permanent magnet 460 is positioned on the elastic carrier element 23. Upon the rotation of the metallic flywheel 400, induction currents are set off by the permanent magnet 460 and their magnetic field works against the magnetic field of the permanent magnet, so that the motion of the flywheel 400 is braked.

An imbalance 29 can, in addition, be positioned on the flywheel 400.

The motion of the flywheel 400 can be described by the angle that is formed by the axles 480 and 490.

The motion of the flywheel be described by a differential equation of the type $$\theta'' + a1*\theta' + a2*\theta + a3*\sin(\theta) = a4*\sin(\omega*t)$$

where the high-placed vertical line signifies the derivation over time. The horizontal rule ω designates the motor's rotation frequency. The constants a1, a2, a3, and a4 are linked with the moment of inertia of the flywheel 400, the mass of the imbalance 29, the gravity acceleration, the spring constant of the spiral spring 440, and the damping constant, which is a result of the braking effect of the permanent magnet 460 on the metallic flywheel 400. The values of these magnitudes can be attuned in such a way that a chaotic course is derived for the angle θ as a function of time, as can be seen in the book *Nonlinear Dynamics and Chaos*, by J. M. T. Thomson and H. B. Steward (New York: John Wiley and Sons, 1986).

In a chaotic deflection of the flywheel 400, the course of the ray path inside the light-conducting fiber 13 is perturbed in corresponding manner, so that the coherence of light is perturbed and this works against the occurrence of speckles at the distal end of the endoscopic system 1.

Figure 7:
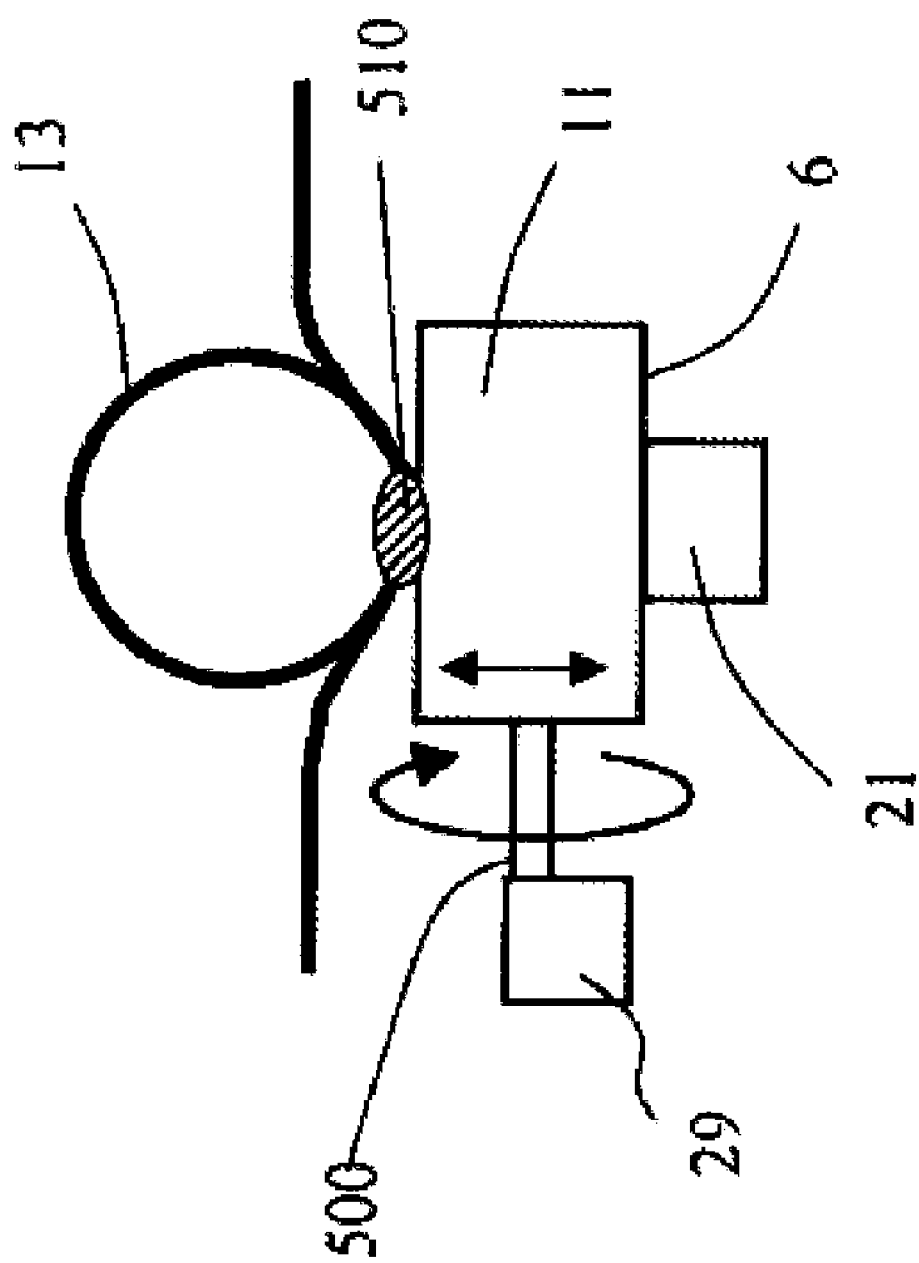
FIG. 7 shows an actuator coupled in material connection to a light-conducting element.

FIG. 7 shows an especially simple embodiment of the coupling of an actuator 11 with a light conductor 13. The actuator 11, which is configured as an electromotor, is positioned on a holder element 21, which is configured as a socket. The light conductor 13 in the form of a glass fiber is cemented directly on the housing 6 of the electromotor 11 by a drop of cement. The electromotor 11 sets an imbalance element 29 in motion by a drive shaft 500, as shown by the bent arrow in FIG. 6. The housing 6 of the electromotor 11 is set in motion through the rotation of the imbalance element 29, so that the directions of rotation are shown by the double arrow. The rotations are transmitted directly onto the glass fiber 13 by the material-locked connection, which is produced by the drop of cement.

Figure 8:
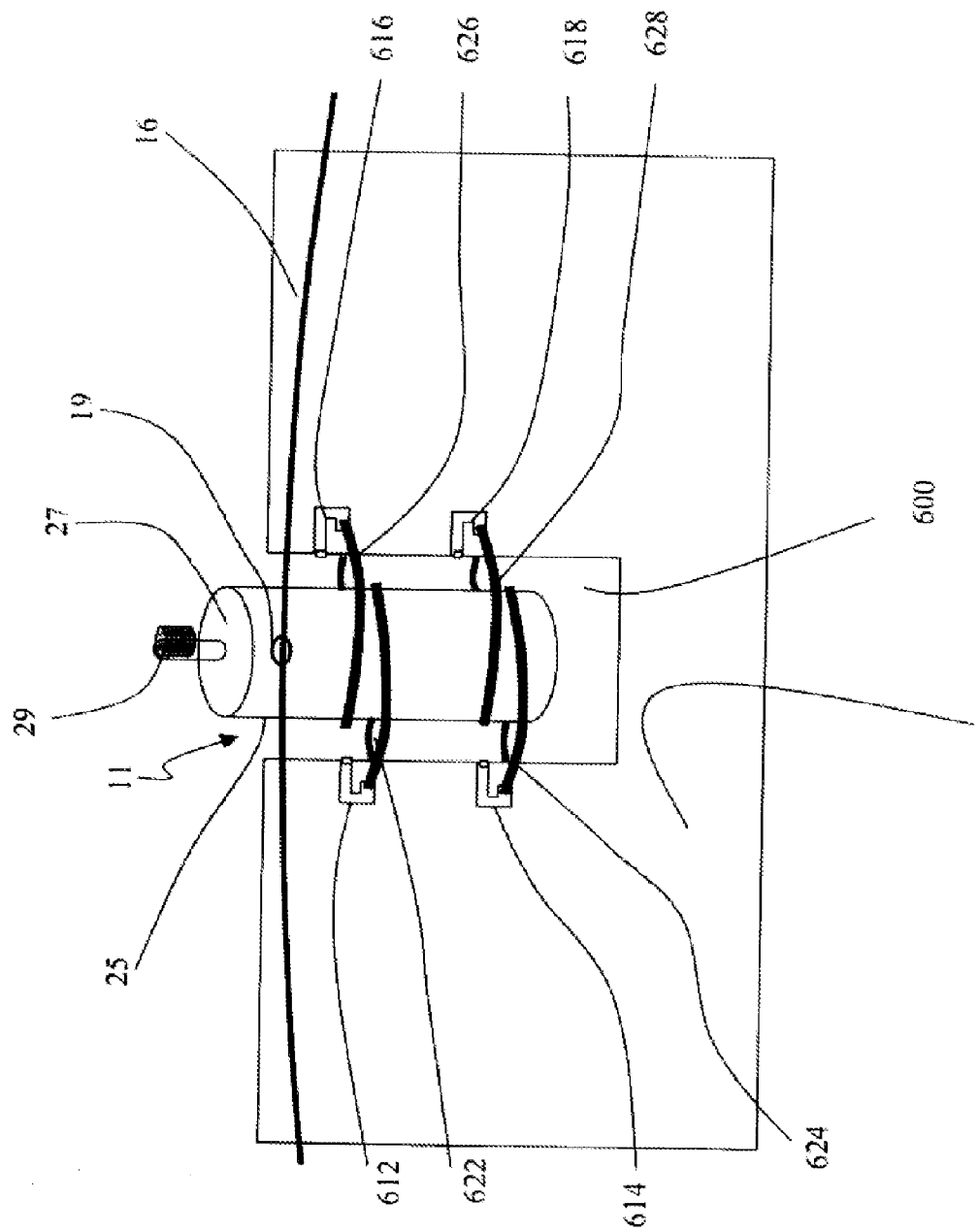
FIG. 8 shows a schematic depiction of suspension of the actuator.

An especially favorable suspension of the actuator 11 is shown in FIG. 8. The holder element 21 of the actuator 11 is configured as a circuit board, which comprises a right-angle recess 600. The circuit board 21 is built into the housing 12 (not illustrated) of the supply unit 10. The recess 600 has on its longer sides slit-shaped fixers 612, 614, 616, and 618, which are placed opposite one another in pairs. The motor 27 of the actuator 11 is held in shaking motion in the right-angle recess 600 of the circuit board 21 by O rings 622, 624, 626, and 628. The O rings surround the housing 25 of the motor 27 and are secured in the fixers 612, 614, 616, 618. The surface of the motor housing 25 includes grooves for better control of the O rings. The imbalance 29 is secured on the rotary axle of the motor 27. A coupling element 19 is soldered onto the motor housing 25 in the form of a metal ring 19. The metal ring 19 surrounds a light-conducting element 13, which is configured as a laser fiber.

As a result of the shifting suspension of the motor 27, the transmission of motor vibrations onto the housing 12 or other components of the proximal supply unit 10 is kept small, so that unintended disturbances of the endoscopic system are to the greatest possible extent avoided.

What is claimed is:

1. An endoscopic or microscopic system for illuminating a surgical area comprising:
   an insertion part, the insertion part including an optical radiance transmission link;
   a proximal supply unit, the proximal supply unit including:
      at least one light source for generating at least partially coherent light, and
      at least one light-conducting element, the at least one light conducting element and the at least one light source positioned in the proximal supply unit; and
   at least one actuator coupled with the at least open light-conducting element and/or with the last one light source,
   wherein the actuator generates aperiodic, chaotic, or stochastic perturbations for reducing speckles.

2. The system of claim 1, wherein the at least one actuator is coupled by a coupling element with the at least one light-conducting element and/or the at least one light source of the endoscopic system in material-locking and/or form-locking and/or force-locking and/or loose connection.

3. The system of claim 2, wherein the coupling element comprises a hole-shaped aperture for passage of the at least one light-conducting element of the endoscopic system.

4. The system of claim 2, wherein the coupling element comprises a damping element.

5. The system of claim 2, wherein the coupling element can be stimulated to rotary spinning motions.

6. The system of claim 1, further comprising at least one fluorescence converter for transforming white light.

7. The system of claim 6, wherein the at least one fluorescence converter is positioned on the distal end of the radiance transmission link in the insertion part.

8. The system of claim 6, wherein the at least one fluorescence converter is positioned in the proximal supply unit.

9. The endoscope of claim 6, wherein the at least one actuator is coupled with at least one fluorescence converter in material-locking and/or form-locking and/or force-locking and/or loose connection.

10. The system of claim 1, wherein the at least one light source for generating at least partially coherent light is a semiconductor laser.

11. The system of claim 1, wherein the at least one actuator is powered by an electronic switch.

12. The system of claim 1, wherein the at least one actuator comprises a piezoelectric converter.

13. The system of claim 1, wherein the at least one actuator comprises a magnetostrictive converter.

14. The system of claim 1, wherein the at least one actuator comprises an electromechanical converter.

15. The system of claim 1, wherein the at least one actuator comprises an imbalance.

16. The system of claim 1, wherein a holder element for mounting the at least one actuator is positioned in the proximal supply unit.

17. The endoscope of claim 1, wherein the at least one light source for generating at least partially coherent light is a diode laser.

18. The endoscope of claim 1, further comprising an eyepiece and/or video camera.

19. An endoscopic or microscopic system for illuminating a surgical area comprising:
   an insertion part, the insertion part including an optical radiance transmission link and at least one fluorescence converter positioned on the distal end of the radiance transmission link;
   a proximal supply unit, the proximal supply unit including:
      at least one light source for generating at least partially coherent light, and
      at least one light-conducting element, the at least one light-conducting element and the at least one light source positioned in the proximal supply unit; and
   at least one actuator coupled with the at least open light-conducting element and/or with the at least one light source,
   wherein the actuator generates aperiodic, chaotic, or stochastic perturbations for reducing speckles, and wherein the at least one actuator is coupled by a coupling element with the at least one light-conducting element and/or the at least one light source of the endoscopic system in material-locking and/or form-locking and/or force-locking and/or loose connection.

* * * * *